(12) United States Patent
Nakagawa

(10) Patent No.: US 7,191,451 B2
(45) Date of Patent: Mar. 13, 2007

(54) MEDICAL SYSTEM WITH A MANAGEMENT SOFTWARE, DATABASE, AND A NETWORK INTERFACE TO PROTECT PATIENT INFORMATION FROM UNAUTHORIZED PERSONNEL

(75) Inventor: Yoshihiro Nakagawa, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 375 days.

(21) Appl. No.: 09/836,222

(22) Filed: Apr. 18, 2001

(65) Prior Publication Data

US 2002/0083215 A1 Jun. 27, 2002

(30) Foreign Application Priority Data

Dec. 27, 2000 (JP) ............................ 2000-397492

(51) Int. Cl.
*G06F 9/44* (2006.01)
*G06F 15/16* (2006.01)
(52) U.S. Cl. .................. 719/317; 709/219; 340/539.12
(58) Field of Classification Search ........ 709/200–203, 709/217–225, 229; 719/320, 317, 314; 707/10, 200; 705/3, 2; 713/186, 182; 382/116; 607/60; 340/539.12; 706/924
See application file for complete search history.

(56) References Cited

U.S. PATENT DOCUMENTS

| 5,899,998 | A | * | 5/1999 | McGauley et al. ...... 707/104.1 |
| 5,991,729 | A | * | 11/1999 | Barry et al. .................... 705/3 |
| 6,004,276 | A | * | 12/1999 | Wright et al. ................ 600/508 |
| 6,108,665 | A | * | 8/2000 | Bair et al. ................ 707/104.1 |
| 6,148,342 | A | * | 11/2000 | Ho ............................. 709/225 |
| 6,182,076 | B1 | * | 1/2001 | Yu et al. ....................... 707/10 |
| 6,256,737 | B1 | * | 7/2001 | Bianco et al. .............. 713/186 |
| 6,280,380 | B1 | * | 8/2001 | Bardy ......................... 600/300 |
| 6,302,844 | B1 | * | 10/2001 | Walker et al. .............. 600/300 |
| 6,421,729 | B1 | * | 7/2002 | Paltenghe et al. .......... 709/229 |
| 6,480,745 | B2 | * | 11/2002 | Nelson et al. ................ 607/60 |
| 6,523,009 | B1 | * | 2/2003 | Wilkins ......................... 705/3 |
| 6,542,905 | B1 | * | 4/2003 | Fogel et al. ................ 707/200 |
| 6,564,104 | B2 | * | 5/2003 | Nelson et al. ................ 607/60 |
| 6,564,323 | B2 | * | 5/2003 | Takahashi et al. .......... 713/182 |

(Continued)

FOREIGN PATENT DOCUMENTS

EP 950972 A2 * 10/1999

(Continued)

*Primary Examiner*—Nathan J. Flynn
*Assistant Examiner*—Haresh Patel
(74) *Attorney, Agent, or Firm*—Staas & Halsey LLP

(57) ABSTRACT

An individual information managing device connected to a communication line network, for managing individual information. A disclosure procedure executing section protects an individual information storing section in which information on each individual has been registered and a disclosure procedure storing section in which an information disclosure procedure assigned for each individual by each individual has been registered. The disclosure procedure executing section receives a request for disclosing information on a specific individual, notifies the specific individual that there has been a request for disclosure in a posting procedure that matches the posting procedure to the specific individual stored in the disclosure procedure storing section, and receives an approval for the information disclosure from the individual who has received this posting. The disclosure procedure executing section also authenticates the specific individual in an authentication procedure that matches the authentication procedure of the specific individual stored in the disclosure procedure storing section.

7 Claims, 11 Drawing Sheets

U.S. PATENT DOCUMENTS

| | | | |
|---|---|---|---|
| 6,611,846 B1* | 8/2003 | Stoodley | 707/104.1 |
| 2002/0025062 A1* | 2/2002 | Black | 382/116 |
| 2002/0029157 A1* | 3/2002 | Marchosky | 705/3 |
| 2002/0038227 A1* | 3/2002 | Fey et al. | |
| 2002/0065685 A1* | 5/2002 | Sasaki et al. | |
| 2002/0083192 A1* | 6/2002 | Alisuag | 709/237 |
| 2003/0135095 A1* | 7/2003 | Iliff | |
| 2003/0140044 A1* | 7/2003 | Mok et al. | 707/10 |
| 2003/0177030 A1* | 9/2003 | Turner et al. | |

FOREIGN PATENT DOCUMENTS

| | | |
|---|---|---|
| JP | HEI 07-141442 | 6/1995 |
| JP | HEI 08-255150 | 10/1996 |
| JP | HEI 10-207964 | 8/1998 |
| JP | HEI 11-53668 | 2/1999 |
| JP | HEI 11-149504 | 6/1999 |
| JP | 2000-251006 | 9/2000 |

* cited by examiner

INDIVIDUAL INFORMATION TABLE

| RESIDENT BASIC NUMBER | ADDRESS | NAME | DATE OF BIRTH | SEX | CLASS OF CARE |
|---|---|---|---|---|---|

Fig. 4

| AUTHENTICATION DATA TABLE | PASSWORD | FINGERPRINT | VOICEPRINT | DNA | ... |

Fig. 5

INFORMATION DISCLOSURE PROCEDURE TABLE

| DISCLOSURE LEVEL | DISCLOSURE ITEMS | AUTHENTICATION METHOD |
|---|---|---|
| 1 | ADDRESS, NAME,... | (POINTER) |

Fig. 6

NORMAL-TIME AUTHENTICATION TABLE

| PASSWORD | FINGERPRINT | VOICEPRINT |
|---|---|---|

Fig. 7

EMERGENCY-TIME AUTHENTICATION TABLE

| FINGERPRINT | DNA |
|---|---|

Fig. 8

POSTING ORDER TABLE

| PORTABLE TELEPHONE | TELEPHONE | MAIL | ACTING PERSON 1 | ACTING PERSON 2 | ... |

Fig. 9

RIGHT TRANSFER TABLE

| PROTECTOR | CARE-TAKER | ... |

Fig. 10

MEDICAL SYSTEM WITH A MANAGEMENT SOFTWARE, DATABASE, AND A NETWORK INTERFACE TO PROTECT PATIENT INFORMATION FROM UNAUTHORIZED PERSONNEL

BACKGROUND OF THE INVENTION

1. Field of the Invention

The present invention relates to an individual information managing device connected to a communication line network, for managing individual information.

2. Description of the Related Art

In recent years, there has been a rapid progress in the utilization of the Internet that connects between personal computers. For example, in the medical field, a data center for managing electronic medical sheet system has been utilized, and this data center has been accessed through the Internet. Thus, the information management system itself has been changed in various fields.

Under the social environment that has been changing rapidly, there has been an urgent requirement for building up a system that can prevent individual information, like individual medical information in the electronic medical sheet system, from being carelessly disclosed or made open through the Internet, thereby to avoid giving unexpected disadvantages to the individuals.

SUMMARY OF THE INVENTION

In the light of the above situation, it is an object of the present invention to provide an individual information managing device that protects individual information.

In order to achieve the above object, according to the present invention, there is provided an individual information managing device connected to a communication line network, for managing individual information, the device comprising: an individual information storing section in which information on each individual has been registered; a disclosure procedure storing section in which an information disclosure procedure assigned for each individual by each individual has been registered; and a disclosure procedure executing section that receives a request for disclosing information on a specific individual through the communication line network, executes an information disclosure procedure that matches an information disclosure procedure of the specific individual stored in the disclosure procedure storing section, and transmits the information on the specific individual to the communication line network toward the information requesting origin when the information disclosure procedure has been satisfied.

The individual information managing device of the present invention stores in advance an information disclosure procedure assigned for each individual by each individual. In disclosing the information on a certain specific individual, this information is disclosed according to the information disclosure procedure that has been assigned in advance by this specific individual. Disclosure of the information against the will of this individual is prevented. Therefore, it is possible to prevent this individual from being subjected to unexpected disadvantages.

In the individual information managing device of the present invention, it is preferable that the individual information storing section is registered with each individual information that consists of a plurality of ranked pieces of information for each individual, based on the arrangement that each individual assigns a rank to each of the pieces of information that constitute the individual information from among a plurality of ranks, the disclosure procedure storing section is registered with an information disclosure procedure according to each rank assigned within each individual by each individual, and the disclosure procedure executing section receives a request for disclosing information on a specific individual, and executes an information disclosure procedure stored in the disclosure procedure storing section that matches an information disclosure procedure corresponding to a rank of the information on the specific individual of which disclosure request has been received.

Individual information includes various levels of individual information relating to their information disclosure such as individual information of which disclosure does not give little problem, and subtle individual information that should be handled confidentially, like ethnic group, race, mental disorder, religion, etc. that are prescribed in the JISQ 15001.

Therefore, as described above, the individual information for each individual is divided into a plurality of ranks. In disclosing the individual information, the information is disclosed according to an information disclosure procedure corresponding to the information to be disclosed. Based on this arrangement, it is possible to balance between the protection and the disclosure of the individual information in further detail.

The information disclosure procedure for each rank is assigned for each individual by each individual. Therefore, the disclosure of information at any rank without the intention of the individual can be prevented. In this case, the assignment of each rank to each individual information is up to each individual. Therefore, it is possible to protect each individual information based on the way of thinking of each individual and the environment.

Further, in the individual information managing device of the present invention, it is preferable that the disclosure procedure storing section is registered with an information disclosure procedure at a normal time for each individual assigned by each individual, and an information disclosure procedure at an emergency time for each individual assigned by each individual, and the disclosure procedure executing section receives a request for disclosing information on a specific individual, with attached information for identifying a normal time and an emergency time, and executes an information disclosure procedure of the specific individual stored in the disclosure procedure storing section that matches the information disclosure procedure at a normal time or the information disclosure procedure at an emergency time, depending on whether the disclosure request belongs to the normal time or the emergency time.

At an emergency time, for example, when the individual has met an accident and is not in a position to be able to express intention of the information disclosure, it is not suitable to request an information disclosure procedure that is the same as that of the normal time. Therefore, it is preferable that the information disclosure procedure is divided into the one for a normal time and the other for an emergency time, and that, at an emergency time, the information disclosure procedure at an emergency time of each individual assigned in advance by each individual is followed.

Further, in the individual information managing device of the present invention, it is preferable that the disclosure procedure storing section is registered with a posting procedure assigned by each individual for posting to an individual, as a part of an information disclosure procedure for each individual, and the disclosure procedure executing section has a disclosure request posting section that receives a request for disclosing information on a specific individual, posts to the specific individual that there has been a request for disclosing the individual information, in a posting procedure that matches the posting procedure to the specific individual stored in the disclosure procedure storing section, and receives an approval for the information disclosure from the individual who has received this posting, and the disclosure procedure executing section receives an approval for the information disclosure from the disclosure request posting section, and further proceeds with the information disclosure procedure.

As a part of the information disclosure procedure, this procedure includes a procedure that, when there has been a request for disclosing the information of a certain individual, the fact that there has been a request for disclosing the information of this individual is posted to this individual, and an approval for the information disclosure is obtained from this individual. Based on this arrangement, it is possible to avoid such a situation that the own information of an individual is disclosed while this individual is not aware of this fact.

Further, in the individual information managing device of the present invention, it is preferable that the disclosure procedure storing section is registered with an authentication procedure assigned by each individual for authenticating each individual, as a part of an information disclosure procedure for each individual, and the disclosure procedure executing section has an authenticating section that receives a request for disclosing information on a specific individual, and authenticates the specific individual in an authentication procedure that matches the authentication procedure of the specific individual stored in the disclosure procedure storing section.

In disclosing the individual information, it is preferable to obtain the approval for the information disclosure from this individual, and to confirm that the approved person is the true individual, based on an authentication procedure. It is possible to reflect the intention of the individual into the authentication procedure along the authentication procedure assigned in advance by the individual.

When both the disclosure request posting section and the authenticating section are provided, it is preferable that the authenticating section authenticates the specific individual in an authentication procedure that matches the authentication procedure of the specific individual stored in the disclosure procedure storing section, after the disclosure procedure executing section has received an approval for the information disclosure from the disclosure request posting section.

Further, in the individual information managing device of the present invention, it is preferable that the disclosure procedure storing section can be freely registered with an authorized person to whom the right of proceeding with an information disclosure procedure on behalf of the individual has been transferred for each individual, and the disclosure procedure executing section receives a request for disclosing information on a specific individual, and executes an information disclosure procedure of the specific individual stored in the disclosure procedure storing section that matches the information disclosure procedure of an authorized person as a procedure for disclosing the information on the specific individual, when the disclosure procedure storing section has been registered with the authorized person to whom the right of proceeding with the information disclosure procedure on behalf of the individual has been transferred.

Based on the above arrangement, a person with parental authority over a child or a protector who looks after a person to be nursed can proceed with the procedure of disclosing the individual information of this cared person while protecting the individual information of this person, on behalf of this person.

BRIEF DESCRIPTION OF THE DRAWINGS

FIG. 4 is a diagram showing an individual-information table that is registered in the individual information storing section.

FIG. 5 is a diagram showing an example of an authentication data table.

FIG. 6 is a diagram showing an example of an information disclosure procedure table.

FIG. 7 is a diagram showing an example of a normal-time authentication table.

FIG. 8 is a diagram showing an example of an emergency-time authentication table.

FIG. 9 is a diagram showing an example of a posting order table.

FIG. 10 is a diagram showing an example of a right transfer table.

DESCRIPTION OF THE PREFERRED EMBODIMENTS

Embodiments of the present invention will be explained below.

Figure 1:
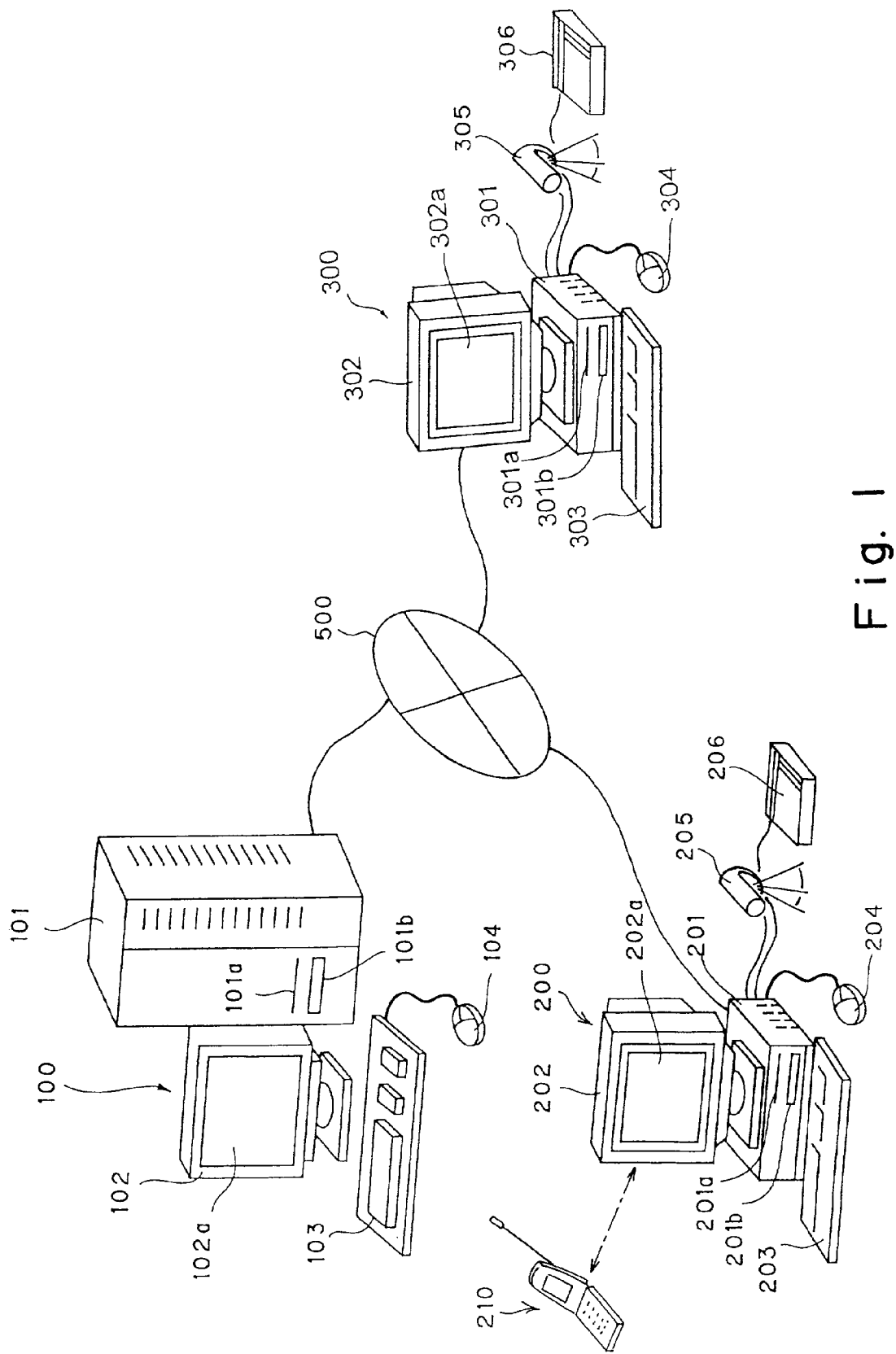
FIG. 1 is a schematic view showing one example of an individual information management and disclosure system that includes one embodiment of an individual information managing device of the present invention.

FIG. 1 is a schematic view showing one example of an individual information management and disclosure system that includes one embodiment of an individual information managing device of the present invention.

This drawing shows one server machine 100 that corresponds to the embodiment of the individual information managing device according to the present invention and two representative client machines 200 and 300. They are connected to a communication line network 500.

Out of the two client machines 200 and 300, one client machine 200 is a client machine at an information provider side. The other client machine 300 is a client machine at an information user side. While one client machine at the information provider side and one client machine at the information user side are shown here, they are shown as representatives. Usually, a large number of client machines at the information provider side and a large number of client machines at the information user side are connected to the communication line network 500.

The client machine 200 at the information provider side is connected with a portable telephone 210. In other words, an electronic mail transmitted to the client machine 200 can be transferred to this portable telephone 210. Also, the portable telephone 210 can make access to this system via the client machine 200. In FIG. 1, an arrow mark may appear to indicate that the portable telephone 210 is directly connected to the client machine 200. However, this arrow mark only shows that the client machine 200 and the portable telephone 210 are connected to each other in the above-described meaning. In actual practice, they are connected to each other via the communication line network 500 including a radio communication line not shown.

The server machine 100 and the two client machines 200 and 300 shown in FIG. 1 include: main body sections 101, 201, and 301 respectively, each incorporating a CPU, a main storage, a hard disk, a communication board, etc.; display sections 102, 202, and 302 respectively for displaying images and character strings on display screens 102*a*, 202*a*, and 302*a* based on instructions from the main body sections 101, 201, and 301 respectively; keyboards 103, 203, and 303 respectively for inputting user instructions to the server machine 100 and the two client machines 200 and 300 respectively; and mice 104, 204, and 304 respectively for inputting instructions corresponding to icons displayed on the screen when an optional position has been assigned on the display screens 102*a*, 202*a*, and 302*a* respectively.

Figure 2:
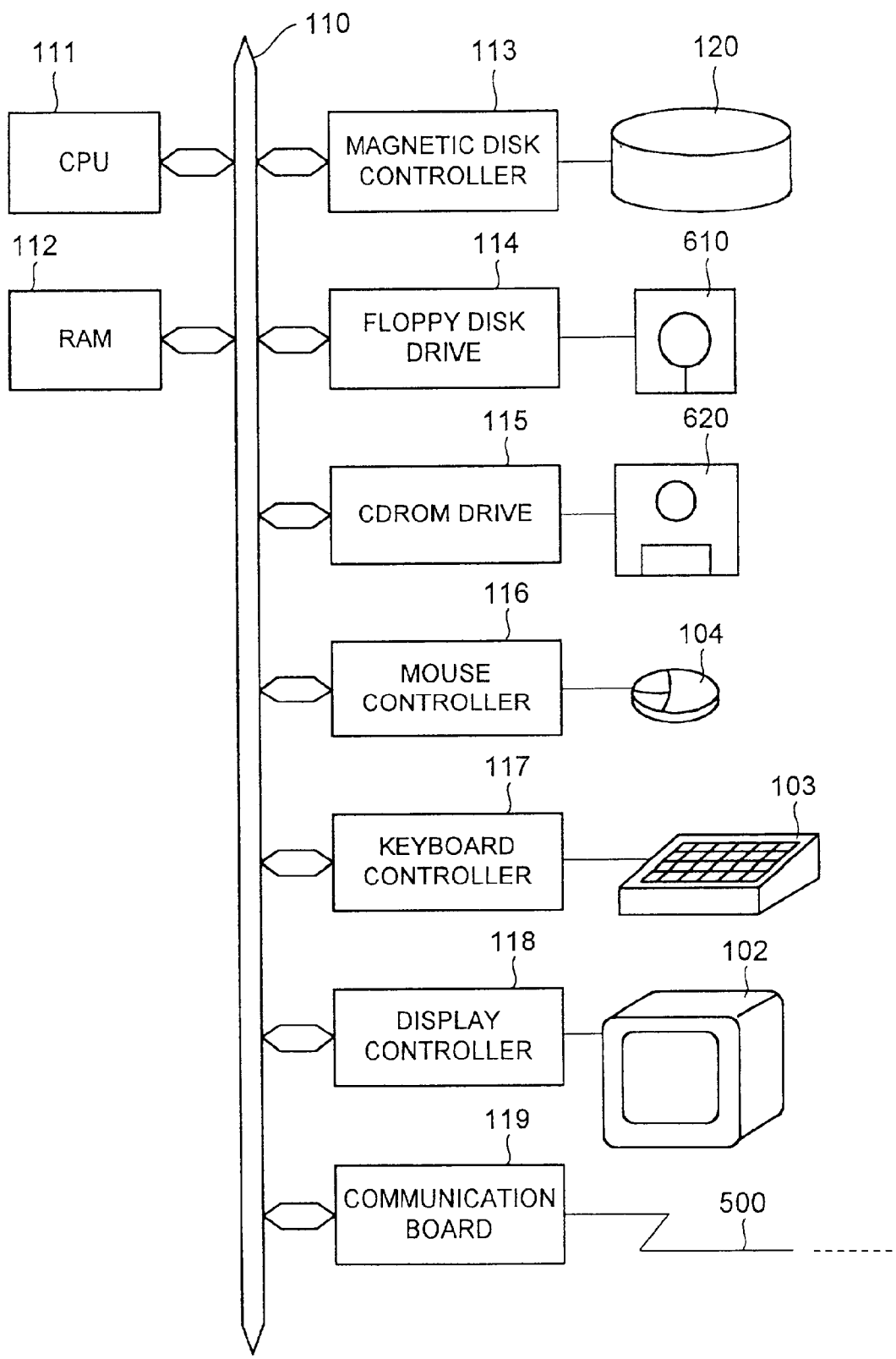
FIG. 2 is a hardware structure diagram of the server machine shown in FIG. 1.

The main body sections 101, 201, and 301 of the server machine 100 and the client machines 200 and 300 respectively further have FD loading openings 101*a*, 201*a*, and 301*a* for loading a floppy disk (FD), and CDROM loading openings 101*b*, 201*b*, and 301*b* for loading a CDROM (an FD and a CDROM are not shown in FIG. 1: reference FIG. 2). Inside these loading openings, there are provided floppy disk drives and CDROM drives for driving the floppy disks and CDROMs inserted from the loading openings 101*a*, 201*a*, and 301*a* and 101*b*, 201*b*, and 301*b* respectively, to make access to the floppy disks and CDROMs. Further, the main body sections 101, 201, and 301 of the server machine 100 and the client machines 200 and 300 respectively are connected to the communication line network 500.

Further, the client machines 200 and 300 are connected with microphones 205 and 305 to input voice, and fingerprint readers 206 and 306 for reading fingerprint respectively.

Further, the portable telephone 210 is connected to the client machine 200 at the information provider side, as described above.

FIG. 2 is a hardware structure diagram of the server machine shown in FIG. 1. Each client machine has a hardware structure similar to that of the server machine, except that the microphone and the fingerprint reader are connected to the client machine. The hardware structure of the server machine will be explained with reference to the drawing.

There are a central processing unit (CPU) 111, a RAM 112, a hard disk controller 113, an FD drive 114, a CDROM drive 115, a mouse controller 116, a keyboard controller 117, a display controller 118, and a communication board 119. They are connected to each other via a bus 110.

The FD drive 114 and the CDROM drive 115 are loaded with a floppy disk 610 and a CDROM 620, for making access to the floppy disk 610 and the CDROM 620 that have been loaded respectively, as explained with reference to FIG. 1.

There are also shown here a hard disk 120 that is accessed by the hard disk controller 113, the mouse 104 that is controlled by the mouse controller 116, the keyboard 103 that is controlled by the keyboard controller 117, the display section 102 that is controlled by the display controller 118, and the communication line network 500 that is connected via the communication board 119.

The CDROM 620 stores an individual information management program for operating the server machine 100 shown in FIG. 1 as one embodiment of the individual information managing device of the present invention. This individual information management program is read from the CDROM 620 by the CDROM drive 115, and is then stored into the hard disk 120 by the hard disk controller 113 via the bus 110. In the actual execution, the individual information management program within the hard disk 120 is loaded onto the RAM 112, and is executed by the CPU 111.

Figure 3:
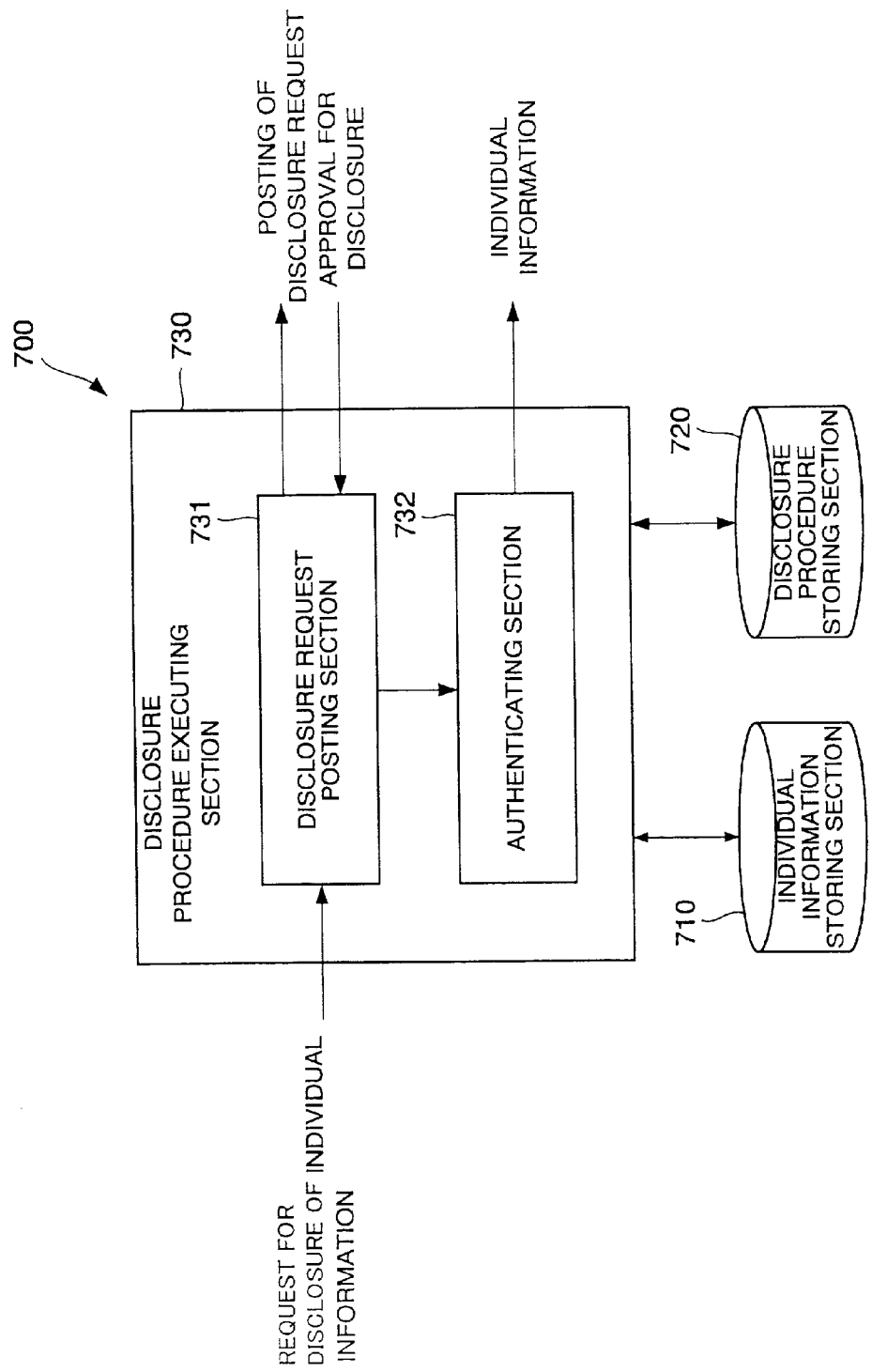
FIG. 3 is a functional block diagram showing one embodiment of the individual information managing device according to the present invention.

FIG. 3 is a functional block diagram showing one embodiment of the individual information managing device according to the present invention. The individual information managing device shown in FIG. 3 is composed of a combination of the hardware of the server machine 100 shown in FIG. 1 and FIG. 2 and the individual information management program installed from the CDROM 620, and the accumulation of the individual information thereafter.

The individual information managing device 700 shown in FIG. 3 consists of an individual information storing section 710, a disclosure procedure storing section 720, and a disclosure procedure executing section 730. The disclosure procedure executing section 730 further includes a disclosure request posting section 731 and an authenticating section 732.

The individual information storing section 710 is registered with information for each individual.

FIG. 4 is a diagram showing an individual-information table that is registered in the individual information storing section.

FIG. 4 shows only a part of individual information for one person. The individual information storing section stores various individual information including a resident basic number, address, name, date of birth, sex, a care class, etc.

The disclosure procedure storing section 720 shown in FIG. 3 is registered with an information disclosure procedure for each individual assigned by each individual.

FIG. 5 to FIG. 10 are diagrams showing examples of various kinds of tables that are necessary for executing the information disclosure procedure for each individual.

Specifically, FIG. 5, FIG. 6, - - - , and FIG. 10 show an authentication data table, an information disclosure procedure table, a normal-time authentication table, an emergency-time authentication table, a posting order table, and a right transfer table, respectively.

One authentication data table shown in FIG. 5 is prepared for each individual. This authentication data table is registered with various data including, for example, a password, a fingerprint, a voiceprint, DNA, etc. that are necessary for authenticating each individual. This authentication data table is a kind of individual information, and these data may be included in the individual-information table shown in FIG. 4. However, for the sake of the subsequent explanation, the authentication data table is prepared separately from the individual-information table.

One information disclosure procedure table shown in FIG. 6 is prepared for each disclosure level of each individual. This information disclosure procedure table is registered with a disclosure level, disclosure items, and an authentication method. The disclosure level is classified into five ranks from 1 to 5 in the present embodiment. As the rank number becomes larger, the level of secrecy becomes higher. The column of the disclosure items shows items of individual information corresponding to the disclosure level (the disclosure level 1 in the example shown in FIG. 6). The column of the authentication method is registered with an authentication method for disclosing the individual information of the disclosure level. However, in this case, this column is registered with a pointer that indicates the normal-time authentication table shown in FIG. 7 in which the authentication method has been registered.

The information disclosure procedure table shown in FIG. 6 is a table in which the information has been registered based on the idea of the individual while based on a guidance of a standard structure. In other words, what individual information is to be registered for the disclosure level 1 and what authentication method is to be used for disclosing the individual information of the disclosure level 1 are all up to the decision of the individual.

The normal-time authentication table shown in FIG. 7 is also prepared for each disclosure level of each individual like the information disclosure procedure table shown in FIG. 6. Each table is indicated with the pointer in the column of the authentication method in the information disclosure procedure table (reference FIG. 6) for each disclosure level of each individual. The normal-time authentication table for each disclosure level is registered with an authentication procedure for each disclosure level at a normal time of the individual.

In the example shown in FIG. 7, it is meant that the disclosure of the items of individual information listed in the linked information disclosure procedure table (reference FIG. 6) is permitted only when the password, the fingerprint and the voiceprint have coincided with the registered ones, at a normal time.

One emergency-time authentication table shown in FIG. 8 is prepared for each individual. This emergency-time authentication table is registered with an authentication method to be used when the individual cannot express the intention of disclosure/non-disclosure of the information like when the individual has become unconscious and also when the information on the individual has become urgently necessary. In the example shown in FIG. 8, it is meant that the disclosure of the information on the individual is permitted when any one of the fingerprint and the DNA of the individual has been confirmed, at an emergency time. The information of this emergency-time authentication table shown in FIG. 8 is also registered based on the intention of the individual. When the columns of this emergency-time authentication table have been blank or when only a password that cannot guarantee the authentication of the individual has been registered, the information of this individual is not disclosed even when the life of this individual faces crisis, except when there is a legal prescription. A request for the disclosure of information at an emergency time is basically permitted to only limited persons like doctors in an assigned emergency hospital. In the present embodiment, when the authentication method registered in this emergency-time authentication table has been satisfied, all the information are disclosed according to the request. However, even at an emergency time, the information to be disclosed may be limited by arranging such that the information that is not urgently required and that is confidential like a criminal record and family origin, etc. is not disclosed.

The posting order table shown in FIG. 9 is prepared for each individual, and this posting order table is registered with orders of posting methods for posting some information to this individual. Each individual registers the methods into this posting order table based on the intention of the individual. The example shown in FIG. 9 means that a posting is first made to a portable telephone. When it has not been possible to communicate with this portable telephone, a call is made to a separate telephone registered in this table. When it has not been possible to communicate with this telephone, a message is sent by an electronic mail. When there has been no reply even after a predetermined period of time (for example, 15 minutes), a message is sent to an acting person 1. When it has not been possible to communicate with the acting person 1, a message is sent to an acting person 2. A method of posting to the acting person 1 and the acting person 2 is based on posting order tables of the acting person 1 and the acting person 2 respectively that are similar to the posting order table shown in FIG. 9. However, even when the posting order table of the acting person is registered with further acting persons of this acting person, a message is not sent to these further acting persons of this acting person.

The right transfer table shown in FIG. 10 is prepared for an individual who requires this table among the individuals.

For example, when the individual is a child of a predetermined age or younger, this right transfer table is registered with a person with parental authority over this child. When the individual is a person who needs care and the care class of this person is at a predetermined level or above, a protector who looks after this person is registered in this right transfer table.

The explanation will be continued referring back to FIG. 3.

The disclosure procedure executing section 730 basically carries out the following. The disclosure procedure executing section 730 receives a request for disclosing the information of a specific individual via the communication line network 500, and executes an information disclosure procedure that matches the information disclosure procedure of this specific individual stored in the disclosure procedure storing section 720. When this information disclosure procedure has been satisfied, the disclosure procedure executing section 730 extracts the information of this specific individual of which disclosure has been requested, from the individual information stored in the disclosure procedure storing section 710. Then, the disclosure procedure executing section 730 transmits the extracted information to the communication line network 500 toward the request origin. Specifically, the disclosure procedure storing section 720 is registered with a posting procedure assigned by each individual for posting to an individual, and an authentication procedure assigned by each individual for authenticating each individual, as a part of an information disclosure procedure for each individual. The disclosure procedure executing section 730 receives a request for disclosing information on a specific individual. Basically, the disclosure request posting section 731 posts to the specific individual that there has been a request for disclosing the individual information, in a posting procedure that matches the posting procedure to the specific individual stored in the disclosure procedure storing section 720, and receives an approval for the information disclosure from the individual who has received this posting. Next, in the disclosure procedure executing section 730, the authenticating section 732 authenticates the specific individual in an authentication procedure that matches the authentication procedure of the specific individual stored in the disclosure procedure storing section 720. However, a message may be sent to an acting person or a protector who looks after this specific individual, instead of sending the message to this specific individual, and the authentication may be obtained from this acting person or the person who looks after this individual. Details will be explained later. After correctly finishing this authentication procedure, the information of which disclosure has been requested is extracted, and this information is transmitted to the request origin.

One example of the individual information disclosure procedure will be explained below. For the purpose of explanation, it is assumed that a patient having the client machine 200 shown in FIG. 1 at home carries the portable telephone 210 and visits a hospital that is installed with the client machine 300 to consult a doctor.

Figure 11:
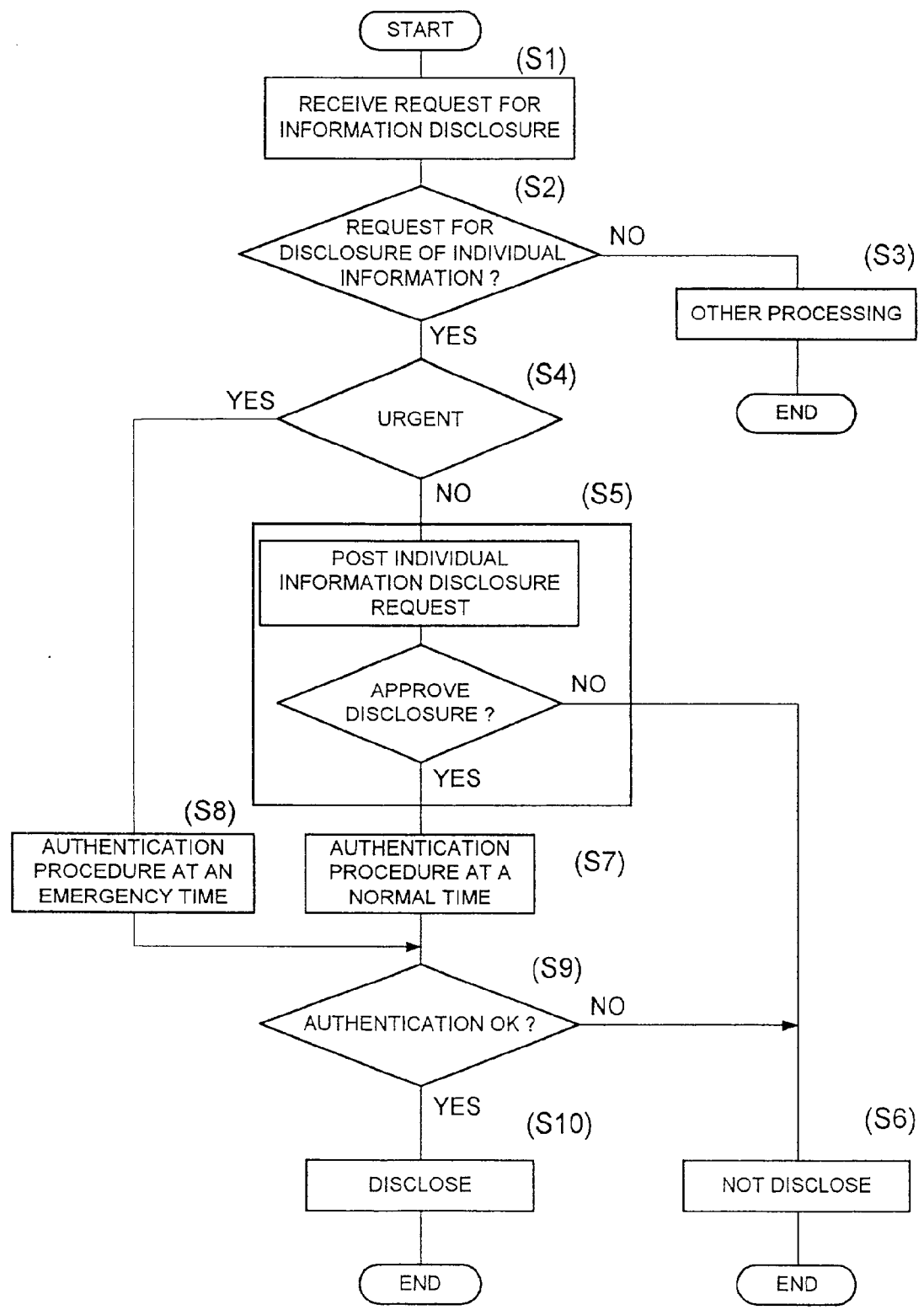
FIG. 11 is a flowchart showing an information disclosure procedure in the server machine.

FIG. 11 is a flowchart showing an information disclosure procedure in the server machine 100 shown in FIG. 2.

A doctor at a hospital installed with the client machine 300 shown in FIG. 1 operates the client machine 300 to request the server machine 100 to transmit information on the case history and the allergy of the visited patient, for the doctor to know this information.

The server machine 100 receives the information disclosure request (step S1 in FIG. 11), and makes a decision about whether this information disclosure request is a request for the disclosure of the individual information according the present embodiment or not (step S2). When the information disclosure request is the request for information irrelevant to the individual information (for example, a guide on the government or a public organization), a processing that meets this characteristic of information is carried out (step S3).

When a decision has been made at step S2 that the information disclosure request this time is the request for the disclosure of the individual information, a decision is made next about whether this disclosure request is urgent or not.

When a decision has been made at step S4 that the information disclosure request is the request at a normal time, the process proceeds to step S5. At step S5, the server machine posts to the owner of this individual information, that is, the patient who has visited the hospital, that there has been the request for disclosing the individual information, and requests this individual (the patient) to approve the disclosure of the individual information. When the patient has not approved the disclosure, the individual information is not disclosed (step S6), and this fact is posted to the disclosure request origin. Details of step S5 will be explained later.

When the patient has approved the disclosure, the process proceeds to step S7, where the authentication procedure at a normal time is carried out. Details of this authentication procedure at a normal time will be also explained later.

When a decision has been made at step S4 that the information disclosure request is urgent, the authentication procedure at an emergency time is carried out (step S8). Details of this authentication procedure at an emergency time will also be explained later.

When the authentication has been carried out correctly in the authentication procedure at step S7 or step S8 (step S9), the requested individual information of this individual (the patient) is disclosed to the request origin (the client machine 300) (step S10). On the other hand, when the authentication has been unsuccessful, the disclosure is not carried out (step S6), and this fact is posted to the request origin.

Figure 12:
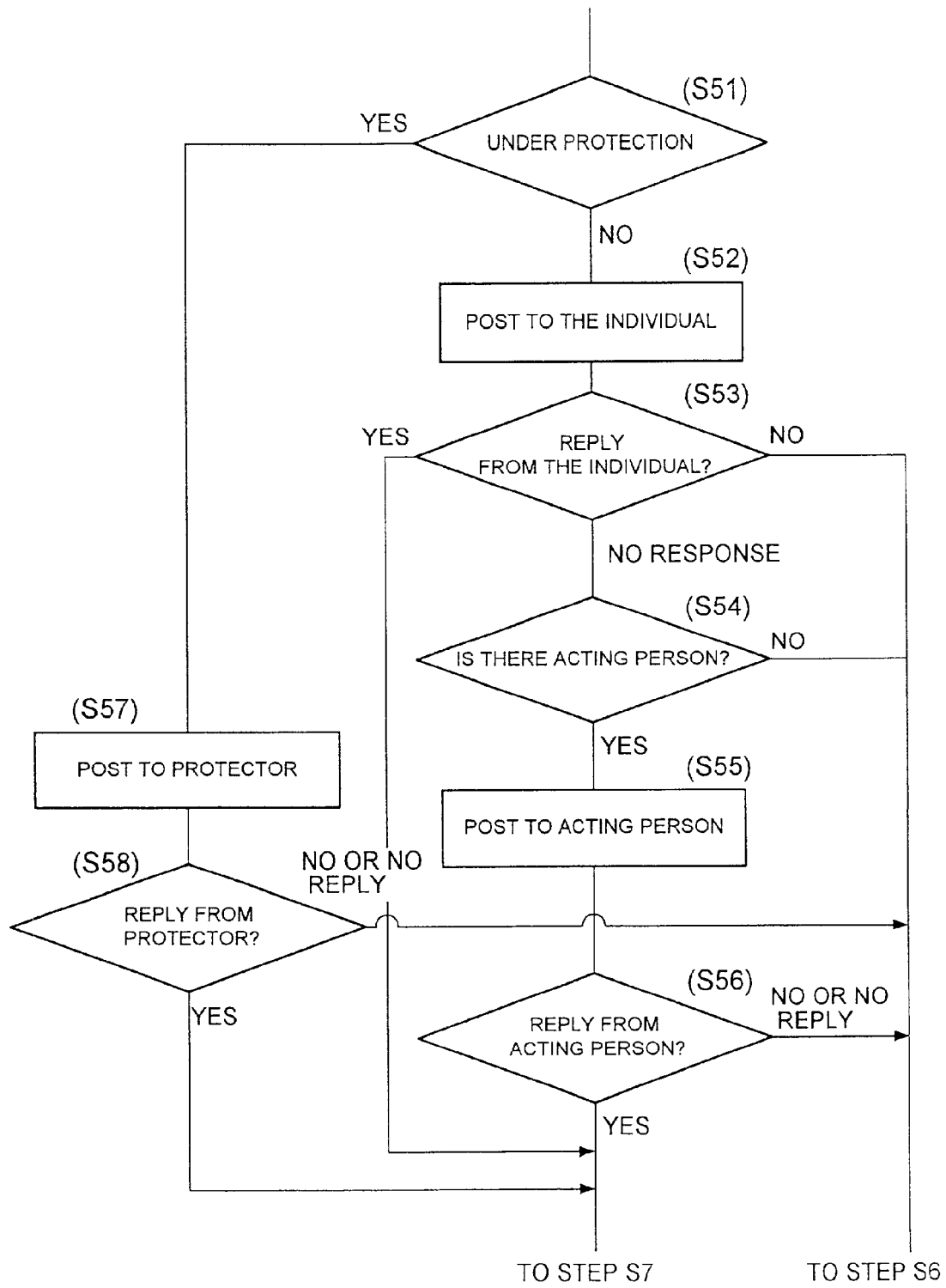
FIG. 12 is a diagram showing a detailed flow of a process of posting an individual information disclosure request and a process of obtaining an approval for the disclosure shown at step S5 in FIG. 11.

FIG. 12 is a diagram showing a detailed flow of the process of posting an individual information disclosure request and the process of obtaining an approval for the disclosure shown at step S5 in FIG. 11.

First, a decision is made about whether the individual as the owner of the information of which disclosure request has been received is under the protection of other individual or not (step S51).

In this case, the individual-information table (reference FIG. 4) of the individual (the patient) as the owner of the information of which disclosure request has been received is referred to. When this individual (the patient) is a child of a predetermined age or younger, or when the individual is a severely handicapped person whose care class is at a high level, a person who looks after this individual is responsible for the disclosure of the individual information. In this case, the right transfer table (reference FIG. 10) of this individual is referred to. Then, the fact that there has been the request for the disclosure of the information of this individual is posted to the protector to whom the right of the disclosure of the information of this individual has been transferred (step S57).

When the individual is a normal adult who does not require such a protection, the fact that there has been the request for the disclosure of the information of this individual is posted to this person (step S52). In posting the message to this person, the posting order table of this person is referred to. In the example shown in FIG. 9, first, the fact that there has been the request for the disclosure of the information of this individual is posted to the portable telephone. When there has been no response from the portable telephone, a posting based on the next step is tried according to the posting order table.

In this case, the patient as the individual who receives this posting has visited the hospital with the portable telephone in hand. Therefore, the portable telephone of this patient receives a call, and the fact there has been the request for the disclosure of the information of this individual is posted in automatic voice. Then, the patient manipulates the buttons of the portable telephone or gives voice to make a response to express the intention of the patient that the patient approves or does not approve the disclosure of the information.

When the server machine 100 (reference FIG. 1) has received a posting from this patient that the patient approves the disclosure, the process proceeds to the authentication procedure at a normal time at the next step S7 (reference FIG. 11). On the other hand, when the server machine 100 has received a posting from this patient that the patient does not approve the disclosure, the process proceeds to step S6 (reference FIG. 11), and a message that the disclosure is not carried out is posted to the client machine 300.

When there has been no response from the individual after the server machine has tried to communicate with this individual through the portable telephone, another telephone, and the electronic mail according to the posting order table shown in FIG. 9, the process proceeds to step S54. At step S54, a decision is made about whether an acting person has been registered in this posting order table or not. When an acting person has been registered, a posting to this acting person is tried (step S55). The posting to this acting person is carried out according to the posting order table registered by this acting person. However, as described above, even when an acting person of this acting person has been registered in the posting order table of this acting person, a posting is not carried to the acting person of this acting person.

When a posting of the approval for the disclosure of the information has come from this acting person as a result of the trial of posting to this acting person of the individual, the process proceeds to step S7. In this case, an authentication procedure is carried out to the acting person who has approved the information disclosure. When a response of no approval for the information disclosure has come from this acting person, or when there has been no response from this acting person (or from none of the acting persons in the case of a plurality of acting persons), the process proceeds to step S6, and the information is not disclosed.

When a decision has been made at step S51 that the individual is under the protection of other individual and the process has proceeded to step S57, a posting is carried out to the protector who looks after this individual according to the posting order table of this protector. In this case, even when an acting person has been registered in the posting order table of this protector, a posting is not carried out to this acting person.

When a response of the approval for the information disclosure has been received from this protector as a result of posting to this protector (step S57), the process proceeds to step S7. In this case, the authentication procedure at a normal time is carried out to this protector. On the other hand, when a response of no approval for the disclosure has been received from this protector or when there has been no response from this protector, the process proceeds to step S6, and the information is not disclosed.

Figure 13:
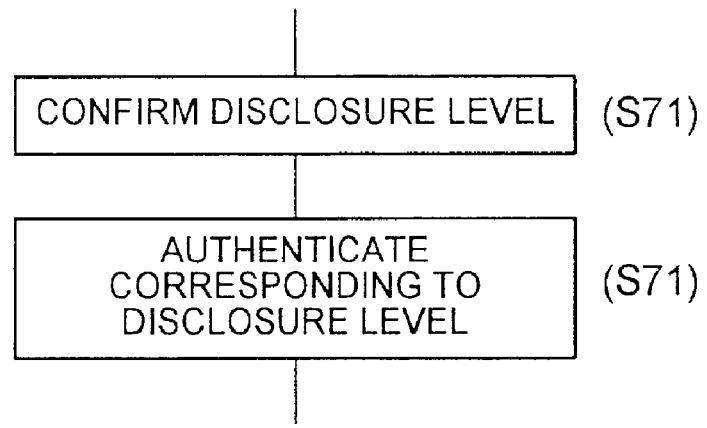
FIG. 13 is a diagram showing a detailed flow of an authentication procedure at a normal time at step S7 shown in FIG. 11.

FIG. 13 is a diagram showing a detailed flow of the authentication procedure at a normal time at step S7 shown in FIG. 11.

The information disclosure table (reference FIG. 6) of the individual (the patient) who has received the information disclosure request is referred to. Then, it is confirmed at what disclosure level the disclosure-requested information has been assigned to (step S71).

Next, the normal-time authentication table (reference FIG. 7) corresponding to the disclosure level of this individual (the patient) is referred to. In this case, when the authentication procedure is carried out to the acting person or the protector in place of the individual, the normal-time authentication table of this acting person or the protector corresponding to this disclosure level is referred to. In this example, the explanation will be continued based on the assumption that the authentication procedure of the individual is carried out.

In the example shown in FIG. 7, it has been registered that the authentication is carried out based on the "password", the "fingerprint", and the "voiceprint". In this case, the server machine 100 requests the client machine 300 to input the password, the fingerprint, and the voiceprint registered in this table. The patient who has visited this hospital inputs the own password from the keyboard of the client machine 300, applies the own fingers on the fingerprint reader 360 to make it read the fingerprint, and further gives voice to the microphone 305 to input the voiceprint. Then, the password, the fingerprint, and the voiceprint are transmitted to the server machine 100 shown in FIG. 1. The server machine 100 compares the password, the fingerprint, and the voiceprint that have been transmitted with the password, the fingerprint, and the voiceprint registered in the authentication data table (reference FIG. 5) of the individual (the patient) respectively, to decide whether they coincide with each other or not.

When it has been decided that the password, the fingerprint, and the voiceprint that have been transmitted from the client machine 300 belong to the individual, the authentication becomes OK. When a decision has been made that any one of the password, the fingerprint, and the voiceprint does not belong to the individual or is unknown, the authentication becomes NG. At step S9 in FIG. 11, a decision is made about whether this authentication is OK or NG.

Figure 14:
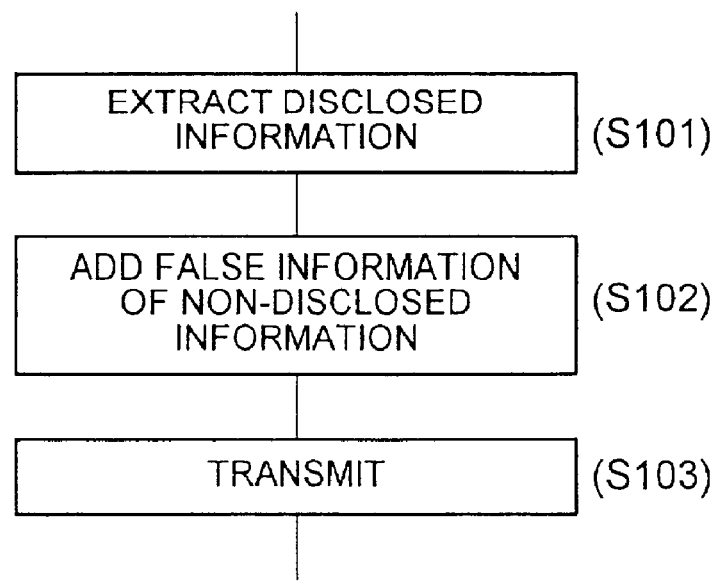
FIG. 14 is a diagram showing a detailed flow of step of a disclosure (step S10) in FIG. 11.

FIG. 14 is a diagram showing a detailed flow of step of the disclosure (step S10) in FIG. 11.

The individual-information table (reference FIG. 4) of this individual (the patient) is referred to, and the disclosure-requested information is extracted (step S101). In the present embodiment, false information is generated for some information of which disclosure has not been requested, and this false information is added to the information extracted from the individual-information table (step S102). Thus, the individual information that partly includes the false information is transmitted to the client machine 300 as the request origin (step S103).

As the client machine 300 knows what information the client machine 300 has requested for the disclosure, the client machine 300 can extract only correct information from the received information that includes the false information. When a human being like the doctor who has operated the client machine 300 tries to discriminate between the correct information and the false information, there is a risk that an unexpected error occurs. Therefore, it is preferable that the client machine 300 stores a record about what information the client machine 300 has requested for the disclosure, extracts only the information of which disclosure has been requested from among the information received from the server machine 100, and presents only the correct information to the doctor. Based on the inclusion of the false information as a part of the information, a malicious third person who steals the individual information in the course of the transmission of the information from the server machine 100 to the client machine 300 cannot discriminate between the correct information and the false information. As a result, it is possible to protect the individual information.

The authentication procedure at an emergency time at step S8 shown in FIG. 11 is carried out, for example, when a patient has become unconscious and has been brought to the hospital.

This hospital has been registered in advance in the server machine 100 as the hospital that performs an emergency medical care. When a special password is input to the client machine 300 installed in this hospital and then the client machine 300 is operated, the server machine 100 can handle the information disclosure request from this client machine 300 as the case of high urgency.

At step S8, the authentication procedure of this case is carried out. At this step, the emergency-time authentication table (reference FIG. 8) of this individual (the patient) is referred to.

In the example shown in FIG. 8, the individual has registered in advance that the authentication is carried out based on the fingerprint or the DNA. The server machine 100 requests the client machine 300 to transmit the fingerprint or the DNA data. The client machine 300 collects the fingerprint of the brought-in patient with the fingerprint reader 306, and transmits this fingerprint to the server machine 100. When the fingers have been disconnected by accident, for example, and it is not possible to use the fingerprint, the DNA analysis is carried out, and this result is input to the client machine 300, and is then transmitted to the server machine 100.

The server machine 100 refers to the authentication data table for this individual (the patient), and makes a decision about whether the transmitted fingerprint is the fingerprint of this individual or not. When the DNA analysis result has been transmitted alternately, the server machine 100 makes a decision about whether this DNA is the DNA of this individual or not. In this authentication procedure at an emergency time (step S8), when it has been confirmed that any one of the items stored in this emergency-time authentication table (reference FIG. 8) belongs to this individual, the authentication becomes OK.

When the authentication has become OK or the authentication has become NG in the authentication procedure at an emergency time at step S8, the subsequent procedure is similar to that after the authentication has become OK or the authentication has become NG in the authentication procedure at a normal time at step S7.

While the explanation has been omitted in the above, the communications between the server machine 100 and the client machines 200 and 300 in the system shown in FIG. 1 are carried out in the encrypted format, and the decryption is made at the received side. The encryption and the decryption are carried out based on the existing techniques.

As explained above, according to the present invention, it is possible to effectively protect the individual information and to effectively utilize the individual information.

What is claimed is:

1. An individual information managing device connected with a communication line network, for managing individual information, the device comprising:
   an individual information storing section in which individual information of each individual is registered;
   a disclosure procedure storing section in which an information disclosure procedure assigned to each individual by each individual is registered, the information disclosure procedure including a plurality of disclosure levels into which the individual information is classified, each disclosure level including disclosure items assigned by the individual and being attached with an authentication method assigned by the individual;
   a disclosure procedure executing section that receives a request from other users for disclosing a piece of individual information of a specific individual through the communication line network, executes an information disclosure procedure of the specific individual stored in the disclosure procedure storing section, and transmits the piece of individual information of the specific individual to the communication line network toward an information requesting origin when the assigned information disclosure procedure is satisfied;
   the individual information storing section is registered with each individual information including a plurality of ranked pieces of information for each individual based on an arrangement that each individual assigns a rank to each of the plurality of ranked pieces of information that constitute the individual information from among a plurality of ranks;
   the disclosure procedure storing section is registered with an information disclosure procedure according to each rank within each individual assigned by each individual; and
   the disclosure procedure executing section receives the request for disclosing the corresponding individual information of the specific individual, and executes an information disclosure procedure stored in the disclosure procedure storing section matching an information disclosure procedure corresponding to a rank assigned to the individual information of the specific individual of which disclosure request is received.

2. The individual information managing device according to claim 1, wherein
   the disclosure procedure storing section is registered with an information disclosure procedure at a normal time for each individual assigned by each individual, and an information disclosure procedure at an emergency time for each individual assigned by each individual, and
   the disclosure procedure executing section receives the request for disclosing the corresponding individual information of the specific individual, with attached information for identifying a normal time and an emergency time, and executes an information disclosure procedure of the specific individual stored in the disclosure procedure storing section matching the information disclosure procedure at a normal time or the information disclosure procedure at an emergency time, depending on whether the request for disclosing belongs to the normal time or the emergency time.

3. The individual information managing device according to claim 1, wherein
   the disclosure procedure storing section is registered with a posting procedure assigned by each individual for posting to an individual, as a part of an information disclosure procedure for each individual, and
   the disclosure procedure executing section has a disclosure request posting section that receives the request for disclosing the corresponding individual information of the specific individual, posts to the specific individual that there has been a request for disclosing the corresponding individual information; in a posting procedure matching a corresponding posting procedure of the specific individual stored in the disclosure procedure storing section, and receives an approval for the individual information disclosure from the individual who received the posting, and the disclosure procedure executing section receives an approval for the individual information disclosure from the disclosure request posting section, and proceeds with the information disclosure procedure.

4. The individual information managing device according to claim 1, wherein
   the disclosure procedure storing section is registered with an authentication procedure assigned by each individual for authenticating each individual, as a part of an information disclosure procedure for each individual, and
   the disclosure procedure executing section has an authenticating section that receives the request for disclosing the corresponding individual information of the specific individual, and authenticates the specific individual in an authentication procedure matching a corresponding authentication procedure of the specific individual stored in the disclosure procedure storing section.

5. The individual information managing device according to claim 1 wherein
   the disclosure procedure storing section is registered with an authentication procedure assigned by each individual for authenticating each individual, as a part of an information disclosure procedure for each individual, and
   the disclosure procedure executing section has an authenticating section that authenticates the specific individual in an authentication procedure matching a corresponding authentication procedure of the specific individual stored in the disclosure procedure storing section, after the disclosure procedure executing section has received an approval for the corresponding individual information disclosure of the specific individual from a disclosure request posting section.

6. The information managing device according to claim 1, wherein the disclosure procedure storing section is freely registered with an authorized person having a right of proceeding with an information disclosure procedure on behalf of the specific individual is transferred for each individual, and the disclosure procedure executing section receives the request for disclosing individual information of the specific individual, and executes an information disclosure procedure of the specific individual stored in the disclosure procedure storing section matching an information disclosure procedure of the authorized person as a procedure for disclosing the corresponding individual information of the specific individual, when the disclosure procedure storing section is registered with the authorized person having the right of proceeding with the information disclosure procedure on behalf of the specific individual is transferred.

7. A method for managing information of users using an information managing device connected with a network, comprising:

storing information of the users in association with information disclosure items, the information disclosure items being correspondingly assigned in accordance with a selection by the users and being provided with authentication methods by the users;

allowing each of the users to define an information disclosure procedure necessary to access respective information of each of the users, the information disclosure procedure including a plurality of disclosure levels into which respective information of the users is classified;

transmitting information corresponding to the information disclosure items of a specific user among the users responsive to an input from other users of an information disclosure procedure matching the assigned information disclosure procedure corresponding to the specific user;

the information of the users includes a plurality of ranked pieces of information for each of the users based on an arrangement that each of the users assigns a rank to each of the plurality of ranked pieces of information that constitute information of each of the users from among a plurality of ranks;

an information disclosure procedure according to each rank assigned by each of the users is registered; and a request is received for disclosing information of said specific user and an information disclosure procedure matching a rank assigned to the information of the specific user is executed.

* * * * *